United States Patent [19]

Hernicz

[11] Patent Number: 4,659,229

[45] Date of Patent: Apr. 21, 1987

[54] READHEAD WITH REDUCED HEIGHT SENSITIVITY

[75] Inventor: Ralph S. Hernicz, Osceola, Ind.

[73] Assignee: Miles Laboratories, Inc., Elkhart, Ind.

[21] Appl. No.: 659,416

[22] Filed: Oct. 10, 1984

[51] Int. Cl.$^4$ ............................................. G01N 21/47
[52] U.S. Cl. .............................................. 356/446
[58] Field of Search .................... 356/445–448, 356/236, 402, 429; 250/228, 227

[56] References Cited

U.S. PATENT DOCUMENTS

| | | | |
|---|---|---|---|
| 3,097,563 | 7/1963 | Weisglass | 250/228 X |
| 3,497,694 | 2/1970 | Jura et al. | 250/227 X |
| 3,718,399 | 2/1973 | Kalman | 356/446 X |
| 4,171,909 | 10/1979 | Kramer et al. | 356/448 X |
| 4,310,249 | 1/1982 | Kramer | 356/236 X |
| 4,395,126 | 7/1983 | Kramer | 356/236 X |
| 4,523,853 | 6/1985 | Rosenbladt et al. | 250/228 X |
| 4,552,458 | 11/1985 | Lowne | 356/446 |

*Primary Examiner*—R. A. Rosenberger
*Attorney, Agent, or Firm*—Roger N. Coe

[57] ABSTRACT

A readhead with reduced height sensitivity for use in a reflectance photometer that measures reflectance of diffuse light from a sample disposed outside the readhead includes a housing with an upper spherical portion and a lower conical portion. The inner peripheral surface of the upper portion is hemispherically configured and the inner peripheral surface of the lower portion is conically configured to permit illumination of a sample disposed outside the readhead. The angle of the cone defined in the conical portion of the housing is in the range of 45°-60°. The inner peripheral surfaces of the upper and lower portions are coated with a highly reflective material, such as barium sulfate. The apex of the conically configured housing portion is truncated to provide a light transmitting aperture for sample illumination. A sample is positioned adjacent the light-transmitting aperture below and outside the conically shaped readhead housing portion. The housing includes a second aperture for receiving a high intensity light from a flash lamp or incandescent light to illuminate the interior of the housing and diffusely illuminate the sample. A baffle is located adjacent the second aperture to avoid direct illumination of the sample. Fiberoptic bundles and photodetectors as well as lenses and reflecting surfaces are provided to detect the amount of diffuse light reflected from the sample.

5 Claims, 4 Drawing Figures

READHEAD WITH REDUCED HEIGHT SENSITIVITY

FIELD OF THE INVENTION

A. Field of the Invention

The present invention relates to reflectance photometers and, more particularly, the present invention relates to diffuse reflectance readheads with reduced height sensitivity.

B. Description of the Background Art

Reflectance photometers commonly are used for quantitative chemical analysis, such as analysis of body fluids, by placing a known quantity of the body fluid on a reactive reagent strip impregnated with a chemical reactive with the quantitatively unknown body fluid component, e.g. blood glucose. The reagent strip is placed within or in contact with a readhead of the reflectance photometer where the strip is illuminated with a controlled, diffuse light and the light reflected from the strip is measured. The reaction product formed on the reagent strip will reflect a known amount of light for each different amount (concentration) of each body fluid component analyzed. Thus, for each different reflection measured from the reagent strip, the quantity of the particular body fluid component in the sample analyzed is known. Some calibration, of course, may be necessary to take into account day to day changes in light source intensity, temperature, and other varying parameters.

Typical reflectance photometers presently used for quantitative chemical analyses include a spherically shaped readhead having an interior diffusely reflecting finish which integrates light for most accurate results. Examples of integrating spheres are disclosed in U.S. Pat. Nos. 4,171,909; 4,310,249 and 4,395,126. Typically, these reflectance photometers are large, expensive and are time consuming to operate since reagent strips must be disposed within or in contact with the integrating sphere for accurate results.

The necessity, in prior art reflectance photometers, for the strip to be within the readhead causes the analyses to be more time consuming since the reagent strips cannot be quickly exchanged, as is possible if the strip analysis position were outside the readhead. A strip analysis position outside the readhead is particularly desirable to perform multiple readings on multiple samples so that a movable sample carrier can be repositioned easily outside the readhead. Further, strip positioning within or in contact with the readhead may cause contamination of the readhead interior surfaces which must be maintained clean so that the surfaces are completely diffusely reflecting.

It has been found that most accurate results in reflectance photometers are obtained when the sample is placed at a point with respect to the readhead where sample illumination is best. For an integrating sphere, the sample must be positioned slightly inside or in contact with the readhead. In accordance with the present invention it has been found that a readhead having a conically shaped portion adjacent the sample position permits the sample to be analyzed from a position outside the readhead while unexpectedly maintaining at least the accuracy of a spherical readhead.

SUMMARY OF THE INVENTION

An object of the present invention is to provide a new and improved readhead for a diffuse reflectance spectrophotometer.

Another object of the present invention is to provide a new and improved readhead for a spectrophotometer capable of more efficient measurements of multiple samples.

A further object of the present invention is to provide a new and improved readhead with reduced height sensitivity for measuring diffuse reflectance from a specimen disposed outside the readhead.

A still further object of the present invention is to provide a readhead that measures the diffuse reflectance of materials placed outside the readhead at least as accurately as less efficient prior art readheads.

Briefly, the present invention is directed to a new and improved spectrophotometer and a spectrophotometer readhead with reduced height sensitivity capable of accurate measurement of reflectance of a sample disposed outside the readhead. The new and improved readhead is useful in conjunction with any known spectrophotometer apparatus that uses a readhead for illuminating a sample and measures reflected light. The spectrophotometer includes a housing with electronic circuitry for powering computing software, a keyboard for inputing instructions and data and a display for displaying information collected. Information is gathered by a readhead defined by a housing with an upper hemispherically shaped portion and a lower conically shaped portion. A high intensity flashlamp is mounted to direct light into the readhead for illuminating samples positioned outside the readhead. Reference and sample fiberoptic bundles, photoelectric detectors and lens assemblies are provided to measure diffuse light reflected from the sample.

BRIEF DESCRIPTION OF THE DRAWINGS

Other and further objects, advantages and features of the invention will be apparent to those skilled in the art from the following detailed description thereof, taken in conjunction with accompanying drawings in which.

DESCRIPTION OF THE PREFERRED EMBODIMENTS

Prior spectrophotometers or reflectance photometers are sensitive to variations in distance between the sample being measured and the readhead (height sensitivity). This height sensitivity limits the utility of these prior art instruments to use with a single sample or reagent strip carefully disposed in a predetermined position within the readhead. Further, the samples and strips disposed within or in contact with the readhead must be most carefully handled to make sure that the solvents and reaction products do not contact the inner surface of the readhead thereby contaminating these surfaces and changing the diffuse reflectance measured.

Figure 1:
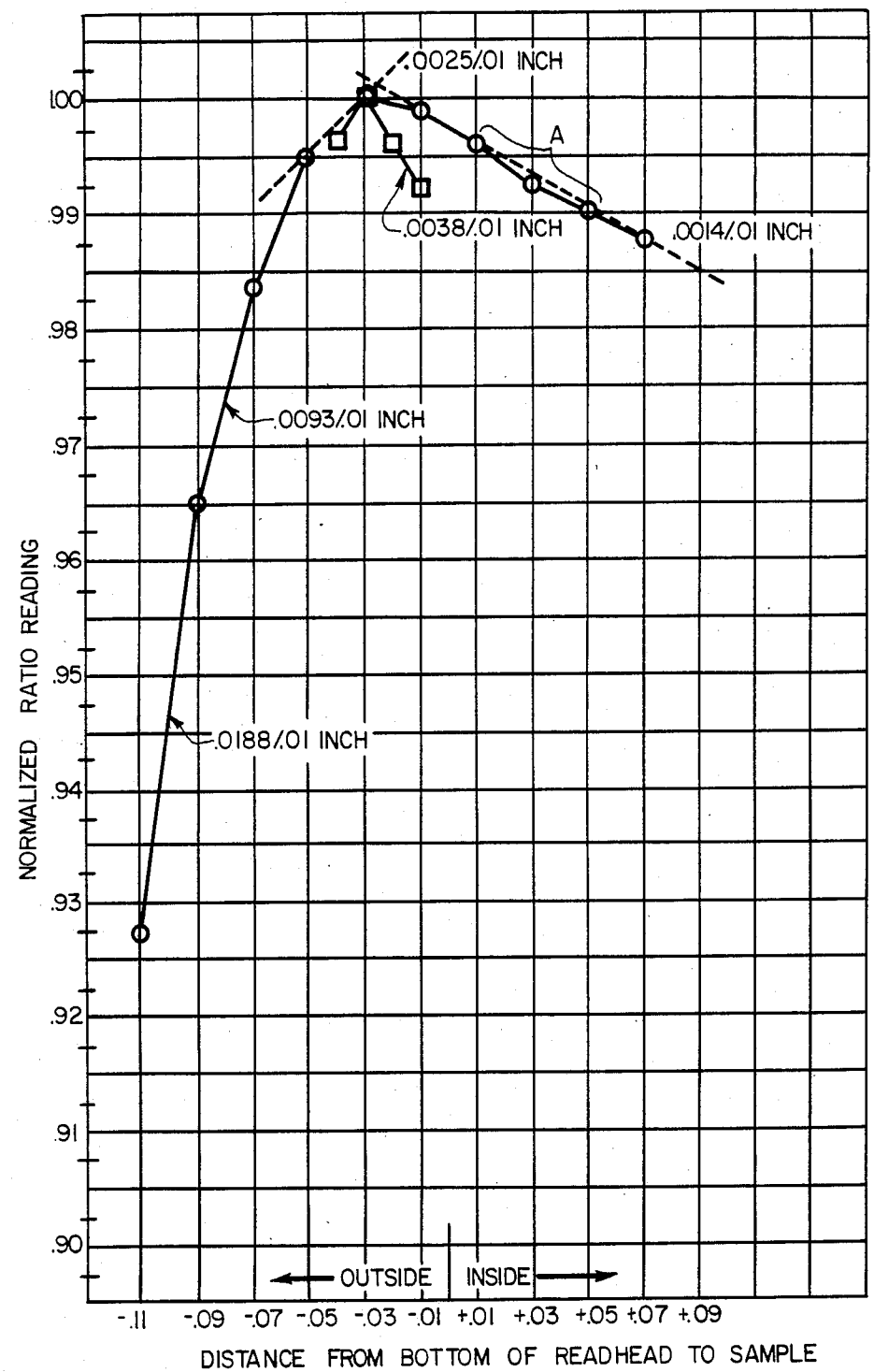
FIG. 1 is a graph illustrating the height sensitivity of a prior art integrating sphere readhead.

FIG. 1 is a graphic illustration of height sensitivity in prior art integrating sphere readheads. In FIG. 1 the vertical axis is the normalized ratio reading (sample channel reading/reference channel reading). The horizontal axis is the distance from the bottom of the readhead to the upper surface of the sample. The negative numbers correspond to distances below and outside the readhead housing and the positive numbers correspond to distances inside the readhead housing.

With readheads of the prior art integrating sphere design, sensitivity can be as high as a 1% change in reflectance for a 0.001 inch change in sample distance from the bottom of the readhead. As illustrated in FIG. 1, the best sensitivity occurs in the area of the plot indicated by the letter "A". This is the portion of the plot with the smallest slope which corresponds to the smallest change in the signal or light from the sample as the distance between the sample and readhead is changed 0.01 inch. In this area, however, the sample is positioned inside the readhead.

Figure 2:
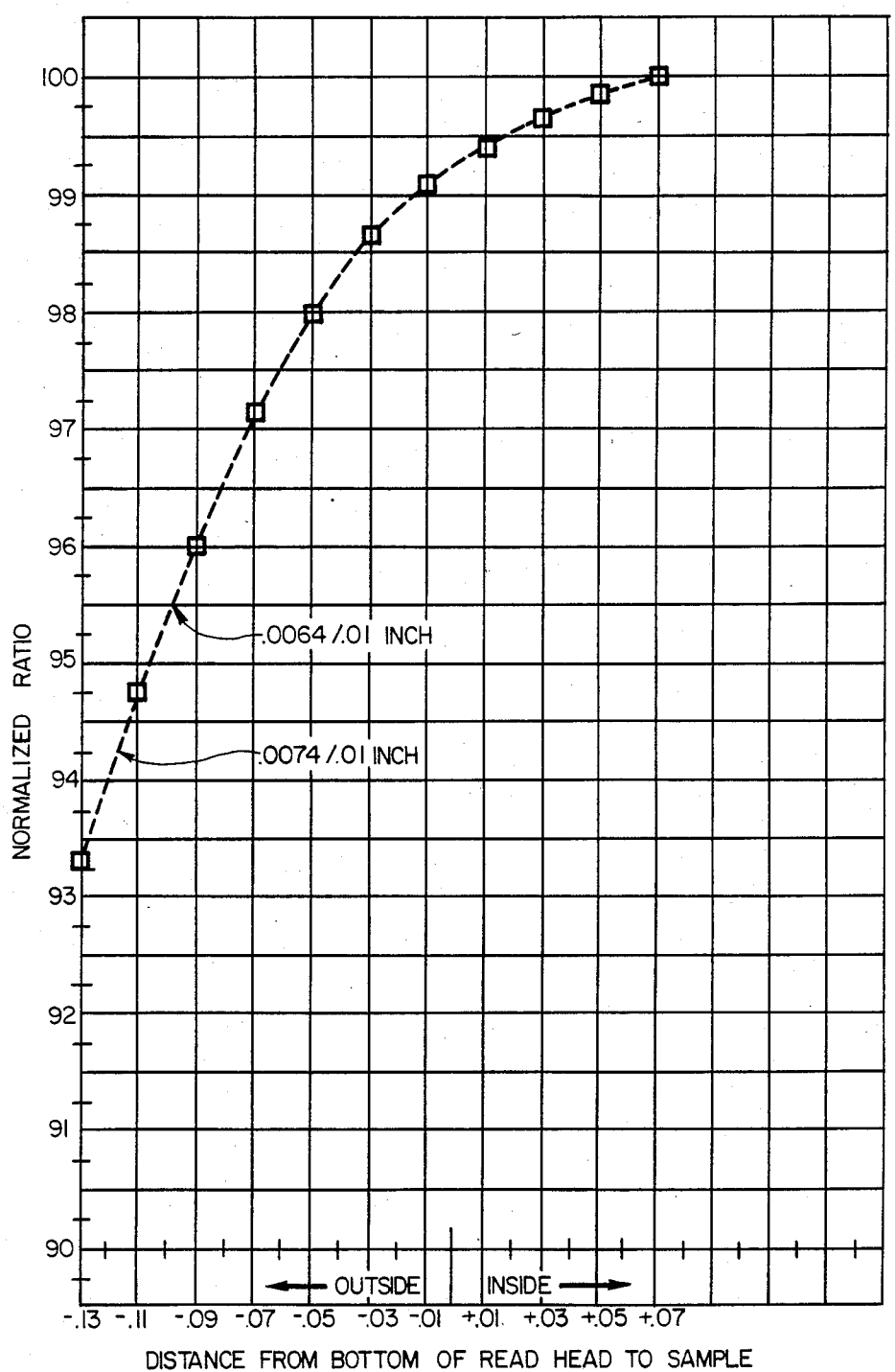
FIG. 2 is a graph illustrating the height sensitivity of a readhead constructed in accordance with the principles of the present invention.

FIG. 2 is a plot of the height sensitivity of a readhead constructed in accordance with the principles of the present invention. As illustrated in FIG. 2, height sensitivity is best with the sample 0.11 inch below the readhead. At this point the slope is 0.0074/0.01, inch versus 0.0188/0.01 at the same location in FIG. 1. This difference illustrates an improvement factor of about three in height sensitivity over the readhead plotted in FIG. 1.

Figure 4:
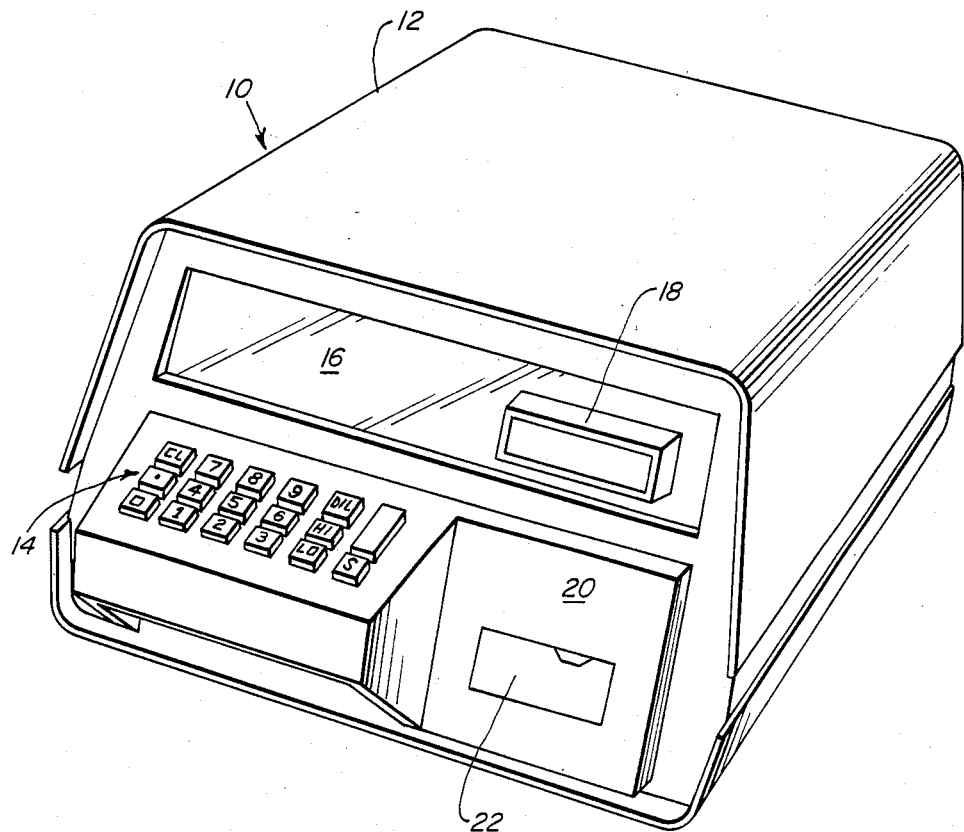
FIG. 4 is a perspective view of a spectrophotometer including the readhead illustrated in FIG. 3.

Turning now to FIG. 4, there is illustrated a spectrophotometer or reflectance photometer generally designated by the reference numeral 10. Spectrophotometer 10 is of the type in which a readhead is used to illuminate a sample with diffuse light. Spectrophotometer 10 senses light reflected from a sample, compares the sample reflected light signal to light received by a reference light sensor disposed within the readhead, and quantitatively determines concentration of a predetermined component in the sample based on the amount of diffuse light reflected from the sample. The quantitative data is displayed on a monitor operatively connected to the light sensing apparatus.

Spectrophotometer 10 includes a housing 12 that, in the preferred embodiment illustrated, is rectangular in configuration with a keyboard 14 for calibration entry and other instructional input. The results of the analysis are displayed on a display monitor 16. Spectrophotometer 10 includes electronic circuitry to power a program module 18 that interprets data collected from the readhead 20 and transmits information to the display monitor 16. A specimen carrier 22 is disposed adjacent the readhead and is disposed to position samples for analysis in a predetermined location with respect to a diffuse light-transmitting aperture in the readhead 20.

Specimen carrier 22 is located approximately 0.11 inch below readhead 20 and can be rotated relative to housing 12 allowing placement of several specimens or samples, one at a time, beneath readhead 20 in a desired sequence. Placement of carrier 22 outside readhead 20 avoids contamination of interior surfaces of the readhead 20 and allows multiple samples to be processed quickly and easily by moving the carrier 22 to position sequentially samples adjacent the diffuse light-transmitting aperture in readhead 20. Readhead 20 reduces height sensitivity and allows accurate measurement of diffusely reflected light from a sample located outside the readhead 20.

Figure 3:
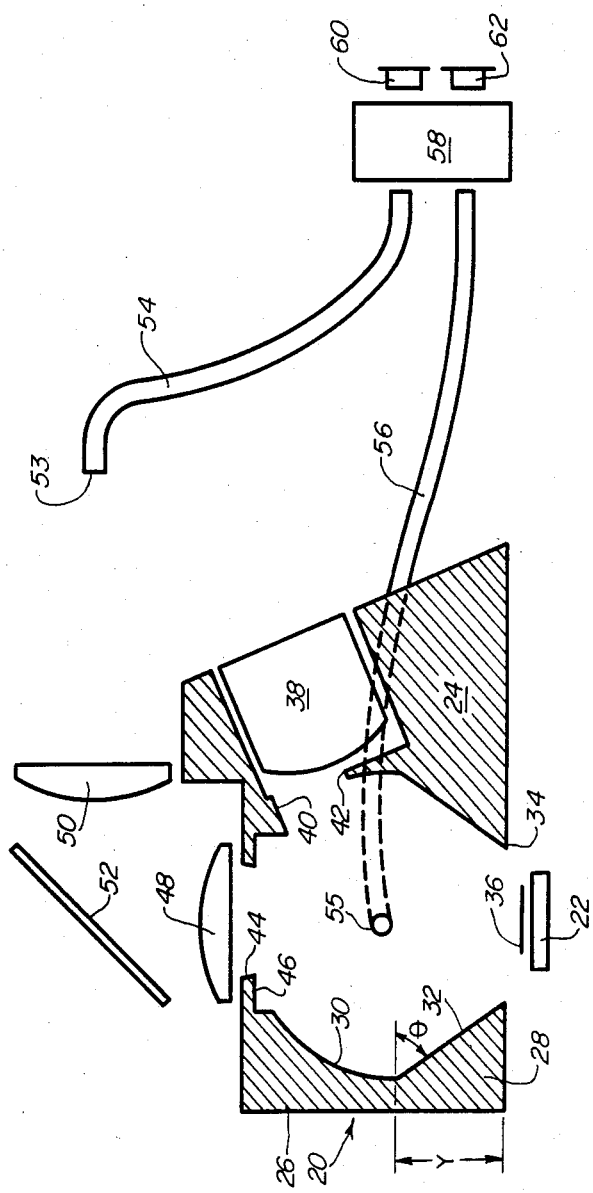
FIG. 3 is a schematic illustration of a readhead constructed in accordance with the principles of the present invention.

A more detailed illustration of readhead 20 is provided in FIG. 3. Readhead 20 includes a housing 24 fabricated of aluminum or any other suitable material. Housing 24 includes an upper housing portion 26 and a lower housing portion 28. Upper housing portion 26 includes a hemispherically configured inner peripheral surface 30 capable of uniformly distributing or diffusing light. Lower housing portion 28 includes a conically configured inner peripheral surface 32 formed with a cone angle $\theta$ measured from a horizontal plane dividing the upper housing portion 26 from the lower housing portion 28, to the cone surface 32. Lower housing portion 28 includes a cone height Y measured from the horizontal plane to the surface of sample aperture 34. Cone height Y should be in the range of 0.5 inch to 1.09 inch. To avoid loss of light and to enhance diffusion, the inner peripheral surfaces 30 and 32 are coated with magnesium oxide, barium sulfate, HALON (polytetrafluoroethylene) available from Allied Chemical Corp., or the like, as well known in the art.

The conical configuration of inner readhead surface 32 has been found to increase light throughput and maintain a constant illumination level on the sample for most accurate reflectance measurement while permitting the sample to be disposed outside the conical housing portion 28. To achieve the full advantage of the present invention, the cone angle $\theta$, as defined, should be 45°-60° and it has been found that particularly unexpected reflectance measuring accuracy is obtained at a cone angle $\theta$ of 50°-60°, particularly at a cone angle $\theta$ of about 55° with a cone height of 0.7 inch. The data of FIG. 2 were gathered with a readhead 20 having a cone angle $\theta$ of 55°.

The conically shaped lower housing portion 28 is cut off or truncated at the apex to provide a light-transmitting sample aperture 34. The diameter of aperture 34 is a function of cone angle $\theta$ and cone height Y. The preferred range of diameters is 0.06 inch to 1.2 inch. At a cone angle of 55° and cone height of 0.7 inch the diameter is 0.6 inch. A sample 36 disposed on carrier 22 is positioned with respect to the sample aperture 34 such that the upper surface of the sample 36 is approximately 0.11 inch below aperture 34 to achieve a reasonable distance between sample and readhead and have adequate height sensitivity when the cone angle $\theta$ is 55°. This distance of 0.11 inch between the upper surface of sample 36 and the sample aperture 34 varies for different cone angles $\theta$.

Light within readhead 20 is provided by a high intensity flash lamp or a continuous incandescent lamp 38 positioned adjacent an aperture 40 in upper housing portion 26, as well known in the art. Lamp 38 is, for example, a high efficiency bulb-type, Xenon flash lamp available as Part No. 9B-3 from EG&G Electro-Optics. Lamp 38 is capable of providing visible and ultraviolet light for endpoint and kinetic determinations.

Baffle 42 is located in front of lamp 38 to prevent direct illumination of sample 36 from lamp 38. This placement of lamp 38 and baffle 42 allows sample 36 to be illuminated entirely diffusely.

Sample 36 is viewed normally through an aperture 44. It is to be understood, however, that placement of apertures 40 and 44 can be in any location in the readhead 20 and the location of the lamp 38 and apertures 40 and 44 is not intended to be limiting to the present invention. The amount of diffuse light reflected from sample 36 will vary depending upon the concentration of a particular component to be measured in sample 36.

Specular light reflected from sample 36, however, contains no quantitative or concentration sample information and is to be avoided since this component could prejudice measurements and result in false reflectance readings. An annular flange 46 surrounding aperture 44 is coated on its inner surface with nonreflecting black material to define a baffle for absorbing the specular component of reflectance from sample 36 allowing only the diffuse component of reflectance to pass through aperture 44.

In order to measure the diffuse component of reflectance, a collimating lens 48 and a focusing lens 50 cooperate with a mirror 52, as well known in the art, to form an image of the sample 36 in an input plane 53 of a fiber-optic bundle 54.

A reference fiber-optic bundle 56 receives reflected diffuse light from the readhead 20 for comparative purposes so that any difference in light intensity within the readhead 20 is compensated for in the computation of reflectance from the sample 36. The reference fiber-optic bundle 56 can be disposed anywhere within the readhead 20 (e.g., opening 55) to receive and transmit readhead reference light intensity data.

Both the sample fiber-optic bundle 54 and reference fiber-optic bundle 56 transfer diffusely reflected light from sample 36 and readhead 20, respectively, through a filter 58 to a pair of detectors 60 and 62, as well known in the art. Detectors 60 and 62 are photodetectors such as, for example, detectors available from EG&G Electro-Optics as Part No. UV-250-B. Information from detectors 60 and 62 is correlated by internal electronics in module 18 and displayed on display monitor 16 (FIG. 4).

From the foregoing, it will be seen that this invention attains all of the ends and objects above set forth. The spectrophotometer 10 described is able to measure reflectance from sample 36 when the sample 36 is disposed outside readhead 20. Spectrophotometer 10 is operable without contaminating readhead 20 and can measure multiple samples very efficiently, one at a time, without loss of accuracy.

Many modifications and variations of the invention as hereinbefore set forth can be made without departing from the spirit and scope thereof and only such limitations should be imposed as are indicated by the appended claims.

What is claimed is:

1. A reflectance photometer for illuminating a sample with diffuse light and sensing the light reflected from the sample comprising a readhead housing, a light source and light sensing means:

said readhead housing consisting of a hemispherically configured upper portion operatively connected to a truncated conical lower portion in which the vertical height of the truncated conical lower portion ranges from 0.5 to 1.09 inch and wherein the interior angle formed by the truncated conical lower portion and the horizontal plane dividing the hemispherically configured upper portion and the truncated conical lower portion of the housing is between 45° and 60°;

wherein the truncated conical lower portion of said housing includes a light transmitting aperture located at the bottom of said readhead housing and wherein the reflectance photometer had a sample carrier mounted a predetermined distance below said aperture;

wherein said readhead housing includes wall structure defining an aperture for transmission of light into said readhead housing from a light source position outside said housing wherein said wall structure is disposed to prevent said light from directly illuminating sample positioned in said sample carrier; and wherein said readhead housing includes wall structure defining at least one aperture for transmission of light reflected from said sample to light sensing means positioned outside said housing.

2. The reflectance photometer of claim 1 in which interior surfaces of the readhead housing are coated to enhance diffusion.

3. A housing for a reflectance photometer in which the interior surfaces of said housing consists of a hemispherically configured upper portion operatively connected to a truncated conical lower portion in which the vertical height of the truncated conical lower portion ranges from 0.05 to 1.09 inch and wherein the interior angle formed by the truncated conical lower portion and the horizontal plane dividing the hemispherically configured upper portion and the truncated conical lower portion of the housing is between 45° and 60°.

4. The housing of claim 3 which also includes an aperture in the hemispherically configured upper portion for transmission of light.

5. The housing of claim 3 in which the interior surfaces of the housing are coated to enhance diffusion.

* * * * *